United States Patent [19]

Pierce, Jr.

[11] Patent Number: 5,055,480
[45] Date of Patent: Oct. 8, 1991

[54] TOPICALLY ACTIVE OCULAR GEM-DIACYLTHIADIAZOLE SULFONAMIDE CARBONIC ANHYDRASE INHIBITORS

[75] Inventor: William M. Pierce, Jr., Louisville, Ky.

[73] Assignee: Research Corporation Technologies, Inc., Tucson, Ariz.

[21] Appl. No.: 495,552

[22] Filed: Mar. 19, 1990

[51] Int. Cl.$^5$ .................. C07D 285/135; A61K 31/41
[52] U.S. Cl. ..................................... 514/363; 548/141
[58] Field of Search ......................... 548/141; 514/363

[56] References Cited

U.S. PATENT DOCUMENTS

| | | | |
|---|---|---|---|
| 3,985,892 | 10/1976 | Roux et al. | 514/363 |
| 4,305,927 | 12/1981 | Theeuwes et al. | 514/363 |
| 4,438,123 | 3/1984 | Smith et al. | 514/363 |
| 4,483,864 | 11/1984 | Barfknecht et al. | 514/363 |
| 4,483,872 | 11/1984 | Barfknecht et al. | 514/363 |
| 4,619,939 | 10/1986 | Maren | 514/363 |
| 4,629,738 | 12/1986 | Barfknecht et al. | 514/363 |
| 4,636,515 | 1/1987 | Barfknecht et al. | 514/363 |

OTHER PUBLICATIONS

Maren, *Journal of Pharmacology and Experimental Therapeutics*, 1987, 241:56–63.
Maren, Drug Development Research, 1987, 10:255–276.
Maren, et al., *Exp. Eye Research*, 1983, 36:457–480.
Kishida, et al., *Exp. Eye Research*, 1986, 43:981–995.
Katritzky, et al., *J. Med. Chemistry*, 1987, 30:2058–2062.
Pierce, et al., *Research Communications in Chemical Pathology & Pharmacology*, 1985, 50:3–20.
Tinker, et al., *The Journal of Pharmacology and Experimental Therapeutics*, 1981, 218:600–607.

Primary Examiner—Robert Gerstl
Attorney, Agent, or Firm—Scully, Scott, Murphy & Presser

[57] ABSTRACT

This invention relates to compounds of the following formula useful as a carbonic anhydrase inhibitor:

A compound of the formula:

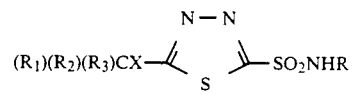

and pharmaceutically acceptable salts thereof wherein
X is $NR_{12}$;
$R_1$ is

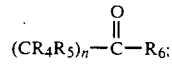

$R_2$ is

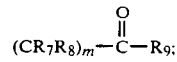

$R_3$ is hydrogen or lower alkyl;
R is hydrogen or lower alkyl;
each $R_4$ and $R_5$ are independently hydrogen or lower alkyl;
each $R_7$ and $R_8$ are independently hydrogen or lower alkyl;
$R_6$ is $OR_{10}$ or $NR_{10}R_{11}$;
$R_9$ is $OR_{13}$ OR $NR_{11}R_{13}$;
$R_{10}$, $R_{11}$ $R_{12}$, and $R_{13}$ are independently hydrogen or lower alkyl; and
n and m are independently 0–6.

37 Claims, No Drawings

TOPICALLY ACTIVE OCULAR GEM-DIACYLTHIADIAZOLE SULFONAMIDE CARBONIC ANHYDRASE INHIBITORS

BACKGROUND OF THE INVENTION

This invention relates to gem-diacyl derivatives of thiadiazole sulfonamides useful as carbonic anhydrase inhibitors (CAI) and pharmaceutically effective salts thereof. More particularly, the compounds of the invention are useful in the treatment of glaucoma and assessment of corneal function.

FIELD OF THE INVENTION

Carbonic anhydrase is an enzyme which secrete acidic or basic fluids found in a variety of tissues including the eye, pancreas, choroid plexus of the central nervous system, kidney, bone and stomach. Carbonic anhydrase medicated secretion is a target for a pharmoca-therapy and a host of pathologies. The compounds of the present invention are useful in the treatment and/or prophylaxis of these pathologies, such as peptic ulcer disease, by inhibiting gastric acid secretion, altitude sickness, epilepsy or as a diuretic.

Another pathological state characterized by inappropriate carbonic anhydrase mediated secretion is metabolic bone disease, such as osteoporosis. The compounds of the present invention inhibit bone resorption and are thus useful for the treatment and/or prophylaxis of metabolic bone disease.

Another pathological state caused by inappropriate carbonic anhydrase mediated secretion is glaucoma. The compounds of the present invention are useful in the management of glaucoma and assessment of corneal function.

The term glaucoma refers to a group of eye diseases often characterized by elevated intraocular pressure (IOP). Accompanying this increased IOP is a restriction of blood supply to the optic nerve and, if uncontrolled, loss of vision. Much of the pharmacotherapeutic management of glaucoma is accomplished by use of agents which are autonomic nervous system agonists or antagonists. The goal of such therapies is reduction in inflow of aqueous humor or improvement of outflow facility.

A class of drugs, the carbonic anhydrase inhibitors (CAI), have been used to diminish aqueous humor inflow by inhibition of carbonic anhydrase (CA). The prototypical acetazolamide (AT) was shown to decrease IOP following oral administration. B. Becker, *Am. J. Opthalmol.*, 38, 16–17 (1954). Findings such as these with other CAI led to a flurry of hopeful research and clinical activity in the preparation of these drugs. The CAI are in general rather non-toxic, and oral administration of CAI does diminish IOP; however, the incidence and severity of side effects have limited patient compliance and hence clinical efficacy. These side effects include depression, fatigue, anorexia and paresthesia. Due to the incidence of these side effects, upon systemic administration of inhibitors, topical administration has been attempted. Under these conditions, however, the most potent CAI (as determined in vitro) do not lower IOP. This is because transcorneal absorption of topically administered CAI yields inadequate drug concentrations in the target tissue—the ciliary epithelium.

Recently, efforts have been renewed in the quest for a topical CAI for the lowering of IOP. Several syntheses have yielded inhibitors which are effective in lowering IOP. See, T. H. Maren, et al. *Exp. Eye. Res.*, 36, 457–480 (1983). One such agent, "aminozolamide", has been tested, and found to be partially effective in clinical trial. See, R. A. Lewis, et al. *Arch. Ophthalmol.*, 104, 842–844 (1986). Other studies have modified methazolamide and ethoxzolamide, which are classical CAI, and have formed compounds having increased corneal permeability. Another approach is the synthesis of prodrugs, e.g., an ester of the hydroxy analog of ethoxzolamide, which is subject to hydrolysis by esterases as it traverses the cornea, yielding an active inhibitor. See, *Exp. Ther.*, 232, 534–540 (1985).

Other groups are developing a new class of CAI which as also effective as an ocular hypotensive agent. See, R. F. Ward, et al., *Abstracts of the Annual Meeting of the American Society for Research in Vision and Ophthalmoloqy*, p16, #7 (1988).

These studies have focused on topical delivery of novel CA inhibitors to diminish systemic side effects. The cornea is a barrier of mixed hydrophobic and hydrophillic properties, due to both cell and stromal layers. Successful penetration of the cornea requires either 1) a drug which of itself has substantial aqueous and lipid solubilities or 2) a prodrug which is lipophilic but is hydrolyzed by cornea epithelial esterases to yield a more hydrophilic active drug.

The endothelium of the cornea is a cell layer on the posterior aspect of the cornea which functions to maintain a dehydrated, transparent cornea. Carbonic anhydrase plays a role in this dehydration function, and inhibition of cornea endothelial carbonic anhydrase leads to transient corneal swelling. Administration of CAI topically to the cornea, followed by measurement of corneal thickness, yields a measure of corneal endothelial functional integrity. From this measurement, the corneal surgeon can differentiate between sufficient and defective corneas and can make a determination whether donor cornea transplant is necessary.

SUMMARY OF THE INVENTION

This invention is directed to novel compounds useful in the treatment of glaucoma or assessment of corneal function having the general formula

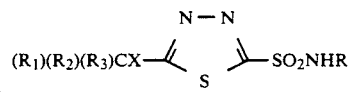

and pharmaceutically acceptable salts thereof wherein
X is $NR_{12}$;
$R_1$ is

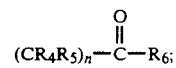

$R_2$ is

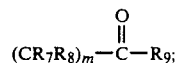

$R_3$ is hydrogen or lower alkyl;
R is hydrogen or lower alkyl;
each $R_4$ and $R_5$ are independently hydrogen or lower alkyl;

each $R_7$ and $R_8$ are independently hydrogen or lower alkyl;
$R_6$ is $OR_{10}$ or $NR_{10}R_{11}$;
$R_9$ is $OR_{13}$ or $NR_{13}R_{14}$;
$R_{10}$, $R_{11}$, $R_{12}$, $R_{13}$ and $R_{14}$ are independently hydrogen or lower alkyl; and
n and m are independently 0–6.

DETAILED DESCRIPTION OF THE INVENTION

The lower alkyl groups, when used singly or in combination with other groups, contain from one to six carbon atoms and may be straight chain or branched. This group includes such groups as methyl, ethyl, propyl, isopropyl, butyl, t-butyl, sec-butyl, isobutyl, amyl, hexyl and the like. In a preferred form the lower alkyl contains from one to four carbon atoms. The most preferred alkyl group is methyl.

In a preferred embodiment, R is hydrogen, thereby defining the $SO_2NH_2$ moiety.

It is preferred that $R_4$, $R_5$, $R_7$ and $R_8$ are all hydrogen. Furthermore, in a preferred embodiment, $R_3$ is hydrogen.

In a preferred embodiment X is NH.

It is preferred that $R_{10}$ and $R_{13}$ are hydrogen or lower alkyl containing 1–3 carbon atoms. It is especially preferred $R_{10}$ and $R_{13}$ are methyl or ethyl.

The preferred $R_6$ and $R_9$ are each hydroxy.

It is also preferred that n is 0, 1 or 2 and m is 1–4. It is most preferred that n is 0 or 1 and m is 1–3.

The compounds of the present invention can be prepared by art recognized procedures For example, compounds of Formula I can be prepared by reacting 2-amino 1,3,4-thiadiazole-5-sulfonamide of Formula II with the corresponding ketone or aldehyde of Formula III under imine forming conditions, followed by reduction of the resulting imine with a reducing agent, such as sodium borohydride, under reducing conditions. These reactions can be Cschematically illustrated as follows:

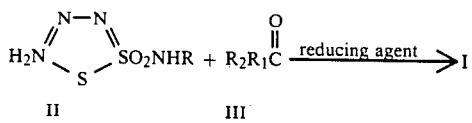

These reactions should be conducted in a solvent in which the reactants are soluble such as water. Moreover, the reactions should be run at temperatures effective for formation of the imines and the reduction thereof.

The 2-amino-1,3,4-thiadiazole-5-sulfonamide described hereinabove is prepared by hydrolysis of acetazolamide with acid or base at reflux temperatures, as described in Example 1.

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmaceutically unacceptable acids are also useful in the isolation and purification of the basic nitrogen-containing new compounds. Salts include those formed with hydrochloric, sulfuric, nitric, perchloric, benzenesulfonic, toluenesulfonic, phosphoric, acetic, malic, malonic, tartaric and similar such acids.

The compounds of the invention also exist in stereoisomeric forms due to the presence of asymmetric centers in the molecule. This invention contemplates the various stereoisomers, i.e., enantiomers or diastereomers, individually or in mixtures such as the racemic mixture. The individual stereoisomers can be obtained by standard resolution procedures known to those skilled in the art or by stereospecific synthesis.

The compounds or compositions of the present invention can be administered to the host in a variety of forms adapted to the chosen route of administration, i.e., orally, topically, intravenously, intramuscularly or subcutaneous routes. The preferred route of administration for ocular use is topical administration to the cornea.

In using the compounds or compositions of this invention for treatment of glaucoma topically, the compound may be carried in an inert, non-eye irritating, non-toxic eye drop diluent of conventional formulation. Such formulations are well known, and commonly referred to in, for example, the Physician's Desk Reference for Ophthalmology (1982 Edition, published by Medical Economics Company, Inc., Oridell, N.J.), wherein numerous sterile ophthalmologic ocular solutions are reported, e.g., see pp. 112-114, which are incorporated herein by reference. For example, the drug may be dissolved in a buffer containing a preservative and a viscosity agent, such as hydroxyalkylcellulose, such as hydroxyethylcellulose hydroxypropylmethylcellulose or saline solution.

Preferably the amount of the carbonic anhydrase inhibitors present in the eye drop treatment composition is concentration of from about 0.25% to about 5% by weight of the eye drop treating composition. Most preferably, the amount is from about 0.5% to about 2.0% by weight of the eye drop treating composition.

As heretofore mentioned, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 5.0 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride. Other anti-bacterials can also be used, such as, for example, chlorobutanol. The amount of wetting agent can range from 0.01% to 0.10%. The amount of anti-bacterial can range from about 0.004% to about 0.02% by weight of the eye drop treating composition.

The compounds of the invention may also be delivered by more sustained delivery devices implanted or apposed directly to the cornea.

The compounds of this invention, are not only water soluble, but they also have a lipid solubility factor to allow transfer across the eye, and they have suitable structure to allow them to effectively function in the eye as carbonic anhydrase inhibitors per se, or following metabolic activation. Their water solubility means ease of preparation for topical application, their lipid solubility characteristics mean effectiveness in transfer across the cornea and into the target site (ciliary body).

For treatment of and/or prophylaxis the other pathological conditions discussed hereinabove, such as ostereoprosis, as well as for the treatment of and prophlaxis of glaucoma, the active compound may also be orally administered, for example, with an inert diluent or with an assimilable edible carrier, or it may be enclosed in hard or soft sell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently contain an amount of active compound in such therapeutically useful compositions is such that a suitable dosage will be obtained. Preferred compositions or preparations according to the present invention are prepared so that an oral dosage unit form contains between about 50 and 500 mg of active compound. In a more preferred form, an oral dosage unit will contain from about 50 mg to about 100 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl propylparabens as preservatives, a dye and flavoring such as cherry or orange flavor. Of course, any material used preparing any dosage unit form should be pharmaceutically pure and substantially non-toxic in the amounts employed. In addition, the active compound may be incorporated sustained-release preparations and formulations.

The active compound may be administered in association with a wafer, shield or insert. In these formulations, the compound may be covalently bonded to or physically associated with the wafer, shield or insert.

The active compound may also be administered parenterally. Solutions of the active compound or pharmacologically acceptable salt can be prepared in water suitably mixed with a viscosity agent, e.g., hydroxyalkylcellulose, such as hydroxypropylmethylcellulose or hydroxyethylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersions medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solution, the preferred methods of preparation are vacuum drying and the freeze-drying technique which yield a powder of the active ingredient plus any additional desired ingredient from previously sterile-filtered solution thereof.

The invention is further illustrated by the following examples.

EXAMPLE 1

2-amino-1,3,4-thiadiazole-5-sulfonamide

This is prepared by hydrolysis of the acetamide 2-acetylamino-1,3,4-thiadiazole-5-sulfonamide (acetazolamide). A slurry of 0.2 mol of acetazolamide in 600 mL of methanol is treated with 60 mL 12N HCl. This mixture is heated with stirring to reflux for 6 hours. Reaction progress is monitored using liquid chromatography. If reaction is not completed after 6 hours, another 30 mL of 12N HCl is added, and the mixture held at reflux for 2 hours. Methanol is then removed under reduced pressure. Product is recovered after raising the pH of the suspension to 7 by addition of NaOH at 0° C.–4° C., followed by filtration. Yield is between 85% and 98% of theoretical with 99% purity. $K_I = 40$ nM.

EXAMPLE 2

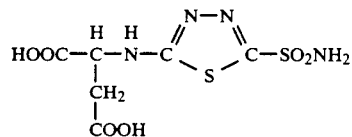

2-Amino-1,3,4-thiadiazole sulfonamide (1 mmol) is dissolved in 5mL H$_2$O. To this solution is added 1 mmol of oxaloacetic acid. Sufficient 4N NaOH is added to raise the pH of the solution to 8. 1 mmol of sodium cyanoborohydride is added and the reaction vessel is sealed. After 16 hours at room temperature, the above product is isolated using anion exchange chromatography.

EXAMPLE 3

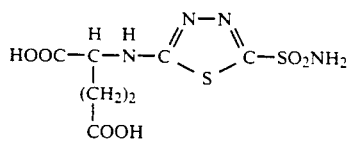

The above product is prepared in accordance with the procedure described in Example 2, except that 2-amino-1,3,4-thiadiazole sulfonamide is reacted with 2-oxoglutaric acid.

EXAMPLE 4

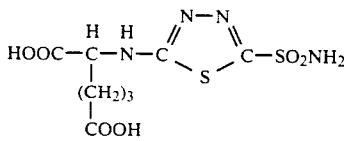

The above product is prepared in accordance with the procedure described in Example 3, except that 2-amino-1,3,4-thiadiazolesulfonamide is reacted with 2-oxoadipic acid.

EXAMPLE 5

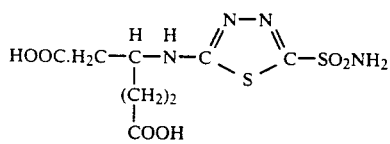

The above product is prepared in accordance with the procedure described in Example 2, except that 2-amino-1,3,4-thiadiazolesulfonamide is reacted with 3-oxoadipic acid.

EXAMPLE 6

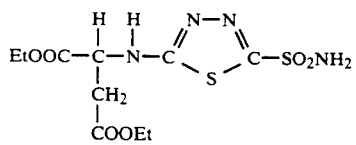

The compound prepared in accordance with Example 2 is reacted with ethylalcohol and $BF_3$/etherate dissolved in ethylalcohol at room temperature. After vacuum stripping the solvent, the crude product is purified by recrystallization in methanol.

EXAMPLE 7

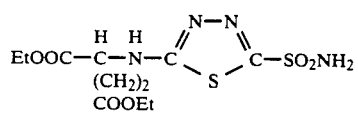

The compound is prepared in accordance with the procedure described in Example 6 except that the product prepared in accordance with Example 3 is utilized.

EXAMPLE 8

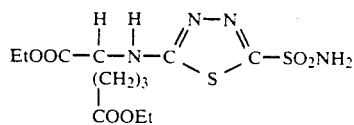

The compound is prepared in accordance with the procedure described in Example 6 except that the product prepared in accordance with Example 4 is utilized.

EXAMPLE 9

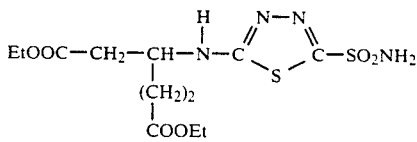

The compound is prepared in accordance with the procedure described in Example 6 except that the product prepared in accordance with Example 5 is utilized.

CAI efficacy and potency are assessed using an enzymatic method. The enzymatic assay is a modification of Maren's micromethod, *J. Pharmacol. Exp. Ther.*, 130, 26–29 (1960). Essentially, a reaction volume of 0.8 mL containing a carbonate/bicarbonate buffer, phenol red, purified carbonic anhydrase, and inhibitor is maintained at 0° and saturated with $CO_2$ by constant bubbling. The time required for acidification to a color change endpoint is monitored as the dependent variable. Carbonic anhydrase inhibitors increase reaction time in proportion to their concentrations over a useful range. Relative potencies are shown in Table I.

TABLE I $$R_1R_2C-\underset{H}{\underset{|}{N}}-\underset{H}{\underset{|}{C}}-\underset{S}{\overset{N-N}{\diagup\diagdown}}C-SO_2NH_2$$

| $R_1$ | $R_2$ | Relative CA inhibition Potency |
|---|---|---|
| —$CO_2H$ | —$CH_2CO_2H$ | 48% |
| —$CO_2H$ | —$(CH_2)_2CO_2H$ | 22% |
| —$CO_2H$ | —$(CH_2)_3CO_2H$ | 20% |
| —$CH_2CO_2H$ | —$(CH_2)_2CO_2H$ | 60% |

*acetazolamide control = 100%

Ocular hypotensive effects following topical administration can be determined on test animals as follows:

New Zealand white rabbits can be used to assess the ability of the compounds of this invention to lower IOP. IOP is determined using rabbits familiarized with the Alcon pneumotonometric measurement employed. Drugs are dissolved or suspended in 0.9% saline or a 1% hydroxypropylmethylcellulose gel and instilled into one eye. The contralateral eye receives the vehicle only, thereby serving as a control. Initial screening is accomplished using measurements every 15–30 minutes for 5–6 hours. Statistical analysis can then be performed using Student's t-test for paired data (two-tailed).

EXAMPLE B

Assessment of Corneal Competence

Non-invasive assessment of corneal competence can be accomplished by topical administration of an effective dose of CAI, followed by serial pachymetry measurements of corneal swelling and recovery over a period of 0.5-2 hours.

The cornea is lined on its posterior aspect by an endothelial cell layer. This endothelium serves to maintain corneal clarity, in part due to the action of carbonic anhydrase. Often (e.g., in conjunction with cataract surgery) it would be beneficial to have a functional test for corneal competence. These agents, when applied topically lead to a mild, transient swelling of the corneal which can readily be assessed by pachymtery. A competent cornea will return to normal thickness rapidly, while a compromised cornea (depressed endothelial function) will not recover as rapidly. This compromised patient is then a candidate for immediate corneal transplant, obviating the need for future inevitable surgery.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A compound of the formula:

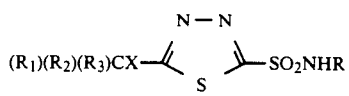

and pharmaceutically acceptable salts thereof wherein
X is $NR_{12}$;
$R_1$ is

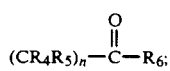

$R_2$ is

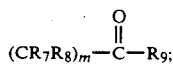

$R_3$ is hydrogen or lower alkyl;
R is hydrogen or lower alkyl;
each $R_4$ and $R_5$ are independently hydrogen or lower alkyl;
each $R_7$ and $R_8$ are independently hydrogen or lower alkyl;
$R_6$ is $OR_{10}$ or $NR_{10}R_{11}$;
$R_9$ is $OR_{13}$ or $NR_{13}R_{14}$;
$R_{10}$, $R_{11}$, $R_{12}$, $R_{13}$ and $R_{14}$ are independently hydrogen or lower alkyl; and
n and m are independently 0-6.

2. The compound according to claim 1 wherein R is hydrogen.

3. The compound according to claim 1 wherein X is NH.

4. The compound according to claim 1 wherein one of $R_4$ and $R_5$ is hydrogen and one of $R_7$ and $R_8$ is hydrogen.

5. The compound according to claim 1 wherein one of $R_4$, $R_5$, $R_6$ and $R_7$ are hydrogen.

6. The compound according to claim 1 wherein n and m are independently 0-3.

7. The compound according to claim 1 wherein $R_3$ is hydrogen.

8. The compound according to claim 1 wherein $R_{11}$ and $R_{12}$ are hydrogen.

9. The compound according to claim 1 wherein $R_6$ and $R_9$ are independently OH.

10. The compound according to claim 1 wherein $R_{10}$ and $R_{13}$ are independently hydrogen or lower alkyl containing 1-5 carbon atoms.

11. The compound according to claim 10 wherein $R_{10}$ and $R_{13}$ are lower alkyl containing 1 to 3 carbon atoms.

12. The compound according to claim 1 wherein R is methyl.

13. The compound according to claim 1 having the formula

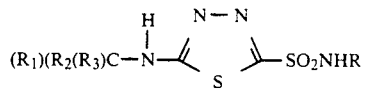

or pharmaceutically acceptable salts thereof wherein
$R_1$ is

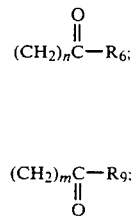

$R_2$ is $(CH_2)_m \underset{\underset{O}{\|}}{C} - R_9;$ $R_3$ is hydrogen or lower alkyl;
$R_6$ is $OR_{10}$ or $NR_{10}R_{11}$;
$R_9$ is $OR_{13}$ or $NR_{13}R_{14}$;
$R_{10}$, $R_{11}$, $R_{12}$ and $R_{13}$ are independently hydrogen or lower alkyl and n and m are independently 0-6.

14. The compound according to claim 13 wherein R is hydrogen.

15. The compound according to claim 13 wherein n and m are independently 0-3.

16. The compound according to claim 13 wherein $R_6$ and $R_9$ are hydroxy or lower alkoxy containing 1 to 3 carbon atoms.

17. The compound according to claim 13 wherein $R_3$ is hydrogen.

18. The compound according to claim 13 wherein R is methyl.

19. The compound according to claim 1 wherein R is H, X is NH, $R_3$ is H, $R_1$ is $CO_2H$ and $R_2$ is $CH_2CO_2H$.

20. The compound according to claim 1 wherein R is H, X is NH, $R_3$ is H, $R_1$ is $CO_2H$ and $R_2$ is $(CH_2)_2 CO_2H$.

21. The compound according to claim 1 wherein R is H, X is NH, $R_3$ is H, $R_1$ is $CO_2Et$ and $R_2$ is $CH_2CO_2Et$.

22. The compound according to claim 1 wherein R is H, X is NH, $R_3$ is H, $R_1$ is $CO_2Et$ and $R_2$ is $(CH_2)_2CO_2Et$.

23. The compound according to claim 1 wherein R is H, X is NH, $R_3$ is H, $R_1$ is $CO_2Et$ and $R_2$ is $(CH_2)_3CO_2Et$.

24. The compound according to claim 1 wherein R is H, X is NH, $R_3$ is H, $R_1$ is $CH_2COOEt$ and $R_2$ is $(CH_2)_2COOEt$.

25. The compound according to claim 1 wherein R is H, X is NH, $R_3$ is H, $R_1$ is $CO_2H$ and $R_2$ is $(CH_2)_3 CO_2H$.

26. The compound according to claim 1 wherein R is H, X is NH, $R_3$ is H, $R_1$ is $CH_2 CO_2H$ and $R_2$ is $(CH_2)_2 CO_2H$.

27. A pharmaceutical composition for the treatment or prophylaxis of pathological disease characterized by an improper carbonic anhydrase mediated secretion comprising a pharmaceutically effective amount of a compound according to claim 1 and a pharmaceutical carrier therefor.

28. A method of treatment or prophylaxis of pathological diseases characterized by improper carbonic anhydrase mediated secretion in mammals which comprises administering to said mammal an effective amount of a compound according to claim 1.

29. The method according to claim 28 wherein the disease is a metabolic bone disease.

30. The method according to claim 29 wherein the metabolic bone disease is osteoporosis.

31. A method of treating glaucoma in mammals which comprises administering to a mammal in need of such treatment an ocular hypotensive effective amount of the compound according to claim 1.

32. The method of claim 31 wherein the compound is dissolved or suspended in a carrier to be administered topically to the eye of the mammal.

33. The method of claim 31 wherein the compound is administered as a wafer, shield or insert directly to the cornea of the mammal.

34. A method of corneal assessment of corneal function in mammals comprising administering to said mammal an effective amount of a compound according to claim 1.

35. The method of claim 34 wherein the compound is dissolved or suspended in a carrier to be administered topically to the eye of the mammal.

36. The method of claim 34 wherein the compound is administered as a wafer, shield or insert directly to the cornea of the mammal.

37. A method for the prophylaxis of glaucoma in mammals comprising administering to said mammal a prophylatically effective amount of a compound according to claim 1.

* * * * *

UNITED STATES PATENT AND TRADEMARK OFFICE
CERTIFICATE OF CORRECTION

PATENT NO. : 5,055,480
DATED : October 8, 1991
INVENTOR(S) : William M. Pierce, Jr.

It is certified that error appears in the above-identified patent and that said Letters Patent is hereby corrected as shown below:

Column 6, lines 48-49: "0° C.-4° C.," should read as --0-4°C,--

Column 9, lines 65-66, Claim 5: delete "one of"

Signed and Sealed this

Fourth Day of May, 1993

Attest:

MICHAEL K. KIRK

*Attesting Officer*     Acting Commissioner of Patents and Trademarks